(12) United States Patent
Hanson et al.

(10) Patent No.: US 8,535,282 B2
(45) Date of Patent: Sep. 17, 2013

(54) WOUND HEALING SENSOR TECHNIQUES

(75) Inventors: Heather S. Hanson, San Antonio, TX (US); Nitin Nitin, Vacaville, CA (US)

(73) Assignee: Southwest Research Institute, San Antonio, TX (US)

( * ) Notice: Subject to any disclaimer, the term of this patent is extended or adjusted under 35 U.S.C. 154(b) by 621 days.

(21) Appl. No.: 12/502,926

(22) Filed: Jul. 14, 2009

(65) Prior Publication Data

US 2011/0015591 A1 Jan. 20, 2011

(51) Int. Cl.
*A61M 1/00* (2006.01)

(52) U.S. Cl.
USPC .......................................................... 604/313

(58) Field of Classification Search
USPC .............. 604/8–10, 313, 319; 435/4, 5, 6.17, 435/286.5, 287.1, 287.5, 288.4, 288.5, 288.7; 422/82.05–82.09, 83, 85–87, 91, 98, 502, 422/503, 507
See application file for complete search history.

(56) References Cited

U.S. PATENT DOCUMENTS

| | | | |
|---|---|---|---|
| 6,080,574 A * | 6/2000 | Berndt | 435/288.7 |
| 6,162,646 A | 12/2000 | Webster et al. | |
| 7,216,651 B2 | 5/2007 | Argenta et al. | |
| 7,327,459 B2 | 2/2008 | Kim et al. | |
| 7,485,266 B2 | 2/2009 | Ito et al. | |
| 7,534,240 B1 | 5/2009 | Johnson | |
| 2004/0038292 A1* | 2/2004 | Burslem et al. | 435/7.1 |
| 2005/0140978 A1* | 6/2005 | Kim et al. | 356/417 |
| 2008/0045807 A1 | 2/2008 | Psota et al. | |
| 2008/0071161 A1 | 3/2008 | Jaeb et al. | |
| 2008/0077091 A1* | 3/2008 | Mulligan | 604/147 |
| 2008/0132819 A1 | 6/2008 | Radl et al. | |
| 2008/0140029 A1 | 6/2008 | Smith et al. | |
| 2008/0271804 A1 | 11/2008 | Biggie et al. | |
| 2010/0217172 A1* | 8/2010 | Hyde et al. | 604/5.01 |
| 2011/0130712 A1* | 6/2011 | Topaz | 604/23 |

FOREIGN PATENT DOCUMENTS

WO 2005078439 8/2005

OTHER PUBLICATIONS

Weingarten et al., "Correlation of near infrared absorption and diffuse reflectance spectroscopy scattering with tissue neovascularization and collagen concentration in a diabetic rat wound healing model," Wound Rep Reg (2008) 16, 234-242 by the Wound Healing Society.*
Definition of "provide", www.thefreedictionary.com/provide.*
Snyder et al., "The Physiology of Wound Healing," Nov./Dec. 2005, Podiatry Management, available at http://www.podiatrym.com/cme/NOV05CME2.pdf, retrieved on Aug. 6, 2009.

(Continued)

*Primary Examiner* — Melanie Hand
(74) *Attorney, Agent, or Firm* — Grossman, Tucker et al.

(57) ABSTRACT

The present disclosure is directed at methods and apparatus to evaluate and monitor healing progress of wound and/or to generate data to modify or identify a treatment protocol. Fluid exudate removed from the wound by a negative pressure therapy device may now be analyzed to identify the progress of wound healing, such as whether healing is progressing in a positive manner or experiencing one or more impediments. The fluid exudates may be specifically analyzed for one or more analytes indicative of one or more of the biochemical reactions that may occur during wound recovery. In addition, one may separately utilize optical sensors integrated into a dressing enclosure, optionally in those dressings employed in a negative pressure therapy device. Such optical sensors may then illuminate the wound and collect information regarding the wound via a light scattering type response.

13 Claims, 1 Drawing Sheet

(56) References Cited

OTHER PUBLICATIONS

Gordillo et al., "Topical Oxygen Therapy Induces Vascular Endothelial Growth Factor Expression and Improves Closure of Clinically Presented Chronic Wounds," Clinical & Experimental Pharmacology & Physiology, 2008, vol. 35, No. 8, pp. 957-964.

Greener et al., "Proteases and pH in chronic wounds," Journal of Wound Care, vol. 14, Iss. 2, Feb. 1, 2005, pp. 59-61.

Rogers et al., "Involvement of Proteolytic Enzymes—Plasminogen Activators and Matrix Metalloproteinases—on the Pathophysiology of Pressure Ulcers," Wound repair and regeneration : official publication of the Wound Healing Society [and] the European Tissue Repair Society 3(3):273-83, 1995.

Mohammad et al., "The in vitro enhancement of rat myofibroblast contractility by alterations to the pH of the physiological solution," European journal of pharmacology, 1998, vol. 357, No. 2-3, pp. 257-259.

Harding et al., "Science, medicine, and the future—Healing Chronic Wounds," BMJ vol. 324, Jan. 19, 2002 pp. 160-163.

Trengove et al., "Analysis of the acute and chronic wound environments: the role of proteases and their inhibitors," Wound Repair and Regeneration, vol. 7, No. 6, Nov. 1999 , pp. 442-452.

Nishimura et al., "Characterization of Optical Parameters with a Human Forearm at the region from 1.15 to 1.52 μm using diffuse reflectance measurements," 2006 Phys. Med. Biol. 51 2997-3011.

Randeberg et al., "Skin Changes Following Minor Trauma," Lasers in Surgery and Medicine 39:403-413 (2007).

\* cited by examiner

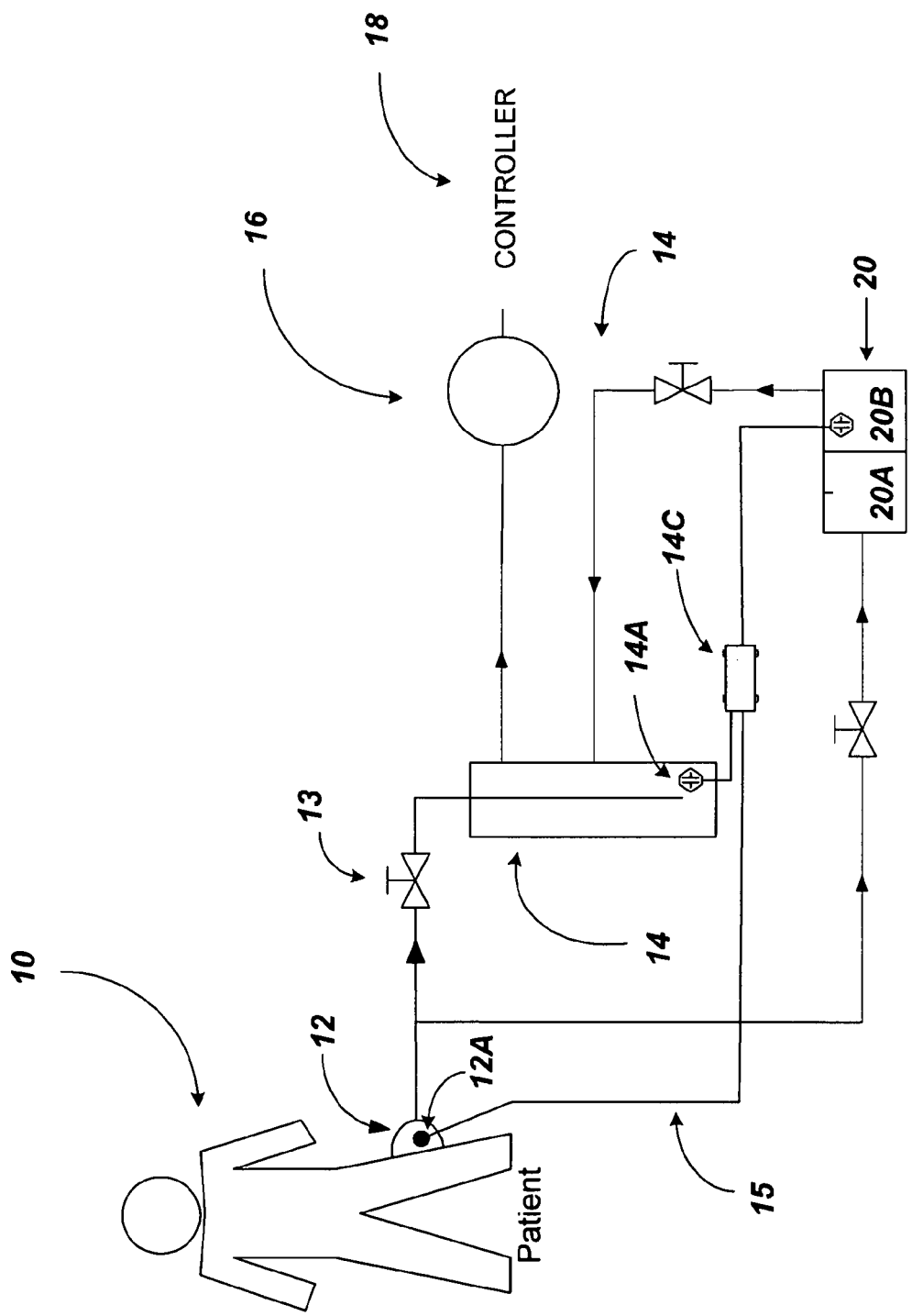

WOUND HEALING SENSOR TECHNIQUES

FIELD OF THE INVENTION

The present invention relates to methods and apparatus for assessing medical progress. More specifically, the present invention relates to methods and apparatus that may be employed to evaluate and monitor the progress of healing in response to a particular dressing or treatment protocol as well as generating data to modify or identify an alternative protocol.

BACKGROUND

Physicians and other medical practitioners often desire a need to evaluate how a particular wound is progressing under a given treatment protocol. When assessing healing, in routine practice, it is often the case that a determination may be visually made on experience and qualitative considerations. In addition, for many wound dressings, it is not possible to evaluate undesirable conditions as they occur, and one may wait several days until the dressing may be removed to identify a given undesirable condition. Accordingly, there is a need to develop more quantitative techniques that may more efficiently identify and predict wound healing progress.

SUMMARY

In a first exemplary embodiment, the present disclosure is directed at an apparatus to evaluate and monitor healing progress of wound and/or to generate data to modify or identify a treatment protocol. The apparatus comprises a dressing enclosure for administering reduced pressure treatment to a wound, wherein the enclosure is configured to cover the wound and to maintain reduced pressure at the wound location. One may then supply a device capable of supplying reduced pressure and a fluid trap connected between the dressing enclosure for the wound and the device capable of supplying reduced pressure to withdraw fluid exudate from said wound. A sensor may then be provided that is capable of analyzing the fluid exudate for one or more analytes indicative of the progress of wound healing.

In another exemplary embodiment, the present disclosure is again directed at an apparatus to evaluate and monitor healing progress of wound and/or to generate data to modify or identify a treatment protocol. The apparatus comprises a dressing enclosure for administering reduced pressure treatment to a wound, wherein the enclosure is configured to cover the wound and to maintain reduced pressure at the wound location. One may then supply a device capable of supplying reduced pressure and a microfluidic device connected between the dressing enclosure for the wound and the device capable of supplying reduced pressure to withdraw fluid exudate from said wound. A sensor may then be provided in the microfluidic device that is capable of analyzing the fluid exudate for one or more analytes indicative of the progress of wound healing.

In another exemplary embodiment, the present invention is directed to an apparatus to evaluate and monitor healing progress of a wound comprising a dressing enclosure, wherein the enclosure is configured to cover the wound. One may then supply an optical sensor in the dressing enclosure, wherein the optical sensor is configured to provide varying wavelengths of light to said wound location and to sense and report any corresponding light scattering. Such an optical sensor may optionally be used with any of the NPTD sensor configurations disclosed herein.

The present disclosure also relates to a method to evaluate and monitor healing progress of wound and/or to generate data to modify or identify a treatment protocol. The method includes locating a dressing enclosure for administering reduced pressure treatment to a wound at a wound location, wherein the enclosure is configured to cover the wound and to maintain reduced pressure at the site of the wound. This may then be followed by supplying a device that provides reduced pressure to the dressing enclosure and locating a fluid trap connected between the dressing enclosure for the wound and the device capable of supplying reduced pressure. One may then withdraw fluid exudate from the wound and supply a sensor capable of analyzing the fluid exudates for one or more analytes indicative of the progress of the wound healing followed by identification of one or more of such analytes.

In addition, the present disclosure also relates to a method to evaluate and monitor healing progress of wound and/or to generate data to modify or identify a treatment protocol. The method includes locating a dressing enclosure for administering reduced pressure treatment to a wound at a wound location, wherein the enclosure is configured to cover the wound and to maintain reduced pressure at the site of the wound. This may then be followed by supplying a device that provides reduced pressure to said dressing enclosure and locating a microfluidic device between the dressing enclosure for the wound and the device capable of supplying reduced pressure. One may then withdraw fluid exudate from the wound and supplying a sensor within said microfluidic device that is capable of analyzing said fluid exudate for one or more analytes indicative of the progress of said wound healing followed by identification of one or more of said analytes.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein:

FIG. 1 illustrates one exemplary configuration of the present disclosure illustrating the use of a negative pressure therapy device in conjunction with various sensors to actively monitor wound healing progression or lack thereof for a given patient.

DETAILED DESCRIPTION

A first aspect of the present invention relates to sampling fluid produced by or in contact with a wound, wherein the sampling may be configured to be continuous thereby providing real-time evaluation of a given wound-treatment protocol. A wound herein may be understood as that situation where skin may be torn, cut or punctured (e.g. an open wound). The wound may also be an internal wound where skin may be cut to insert an internal dressing. Wounds herein may also include both acute and chronic wounds, wherein an acute wound is a wound that is the result of injuries that disrupt the tissue and a chronic wound are those that may be caused by a relatively slow process that leads to tissue damage (e.g., pressure, venous an diabetic ulcers).

More specifically, fluid may be extracted from a wound, which may be facilitated by the use of a negative pressure therapy device (NPTD). A NPTD may be understood as a device that may apply sub-atmospheric pressure (e.g. <760 mm Hg) to a wound location. The wound may be partially or fully covered to facilitate the development of negative pressure at a desired region. Various types of relatively resilient foam surface dressing are typically sealed within an adhesive drape to assist in the formation of vacuum at the wound site.

The use of the NPTD typically provides a variety of advancements in wound management. Among these may include active removal of extra-cellular debris, decrease in peri-wound edema, thereby increasing wound profusion and improving nutrition. In addition, the use of NPTD may also provide wound contracture, decreased bacterial colonization, increased rates of granulation tissue formation and epithealization and stimulation of mitosis and angiogensis.

Attention is therefore directed to FIG. 1, which illustrates one example of a negative pressure therapy device in accordance with the present invention. As can be seen, a patient 10 may have negative pressure applied to a selected wound location which location is surrounded by a fluid tight dressing enclosure 12. The negative pressure may be adjusted to provide a cycle of negative pressure application and relatively constant removal of fluid (subject to available fluid concentration at the selected wound location). In addition, the negative pressure may be adjusted to provide a temporary increase or decrease in the amount of fluid that may be removed from the wound.

For example, when it is desired to evaluate the fluid for the presence or absence of a particular target molecule, bacteria, biomarker (any kind of molecule that may indicate the existence, past or present, of living organisms) or tissue growth factors (e.g. TGF-beta) the negative pressure may be selectively increased or applied for a chosen period of time to secure a fresh sample for analysis. In addition, according to such protocol, it may be appreciated that the extracted wound fluids may provide an indication of target molecules and/or bacteria within a given soft tissue gradient.

For purposes of creating suction within the system the enclosure 12 is connected to a vacuum system generally designated at 16 which provides a source of suction or reduced pressure at the wound site. Valves 13 may be employed to selectively control the application of the negative pressure. A fluid trap/canister is shown generally at 14 that may be connected between the vacuum systems 16 which enable one to collect fluid exudates from the wound for temporary storage or analysis. The fluid trap may optionally contain a sensor 14A integrated in the canister or the sensor may be positioned within the illustrated flow lines 15 or in parallel with such lines or positioned within a microfluidic device 20. Accordingly, one or a plurality of sensors may be used in any particular desired configuration. The sensor(s) may be connected to a computer 14C or other data processing unit. The computer 14C may be integrated within the NPTD such that sensor readings could be used to adjust on-going therapy profiles. Predetermined amounts of suction or reduced pressure may be produced by vacuum system 16 as inputted from the controller 18. The fluid trap may include a float-valve assembly (not shown) which may seal off the suction of the fluid trap when the quantity of fluid in the trap 14 exceeds a predetermined level.

The microfluidic device 20 is specifically capable of providing a closed-channel continuous flow system which contains and manipulates a relatively small amount of fluid within a micro-channel structure. Such micro-channel structure may be produced by micro-processing technology such as photolithography. The device may also be manufactured by metal etching, deposition and bonding, soft lithography, thick-film and stereolithography as well as by relatively fast replicating methods such as electroplating, injection molding and embossing. The flow passages may therefore have a width and depth of 1 µm to 500 µm which may be configured to offer a flow rate at a sensor location of 1 µL/min to 100 µL/min. The microfluidic device 20 may also contain a sensor for sampling of the fluid under consideration.

The sensor herein, which may be utilized within the canister, the flow lines, and/or within the microfluid chip, may be broadly understood as any device that provides analysis of the fluid exuded from or in contact with the wound, which sensor provides information regarding the progress of wound healing. Reference to the progress of wound healing may be understood as determining whether wound healing is progressing in a positive manner towards an orderly healing cascade and/or whether the healing progress is experiencing one or more impediments, such as an increase in bacterial burden which may occur when wounds become critically colonized or infected where organisms may be present at levels of greater than $10^5$ CFU (colony forming units) per gram of tissue. Furthermore, as noted above, the sensor, in combination with computer 14C may now provide the ability for the therapy protocol to be adjusted. Under a negative pressure therapy protocol, the amount or cycling of the negative pressure could be altered. Additionally, antibiotics could be instilled into the wound to address bacterial infections. A lack of wound healing can also suggest the need for additional debridement. Typically, these issues are not known until after the treatment protocol has been completed, which can result in further damage to the wound.

The sensor may therefore rely upon the presence or lack of presence of a given analyte within the exuded fluid or biochemical reactions between specific analytes within such fluids present within the sensor environment (e.g. within the canister 14) that provide a color output, electrical output or other quantifiable reaction whose rate or extent is proportional to the concentration of those analytes that are desired for analysis. Accordingly, the present disclosure allows one, in conjunction with the NPTD, to continuously measure the chemical entities (e.g. analytes) present within wound fluid and for reporting these concentrations and ratios between the various chemical entities during the healing process.

As now may be appreciated, to the extent that it is desirable to continuously monitor a selected analyte within the fluid exudates, one may generally employ a device known as a colorimeter, which may be understood as a device that measures the absorbance of particular wavelengths of light by a specific solution. This may then be utilized to identify the particular concentration of a selected analyte in solution wherein the concentration of the analyte in solution is proportional to the absorbance. A critical determination may then be made for predicting the course and probability of successful healing within an interval acceptable to patients and their care providers, so that the most appropriate and cost-effective treatment may be selected.

For example, one may elect to specifically monitor oxygen levels within a fluid exudate and/or fluid pH. One may therefore rely upon colorimetric and/or fluorescence change along with LED excitation and an optical detector. In addition, one may include oxygen and/or pH sensitive chromophores in the exudates fluids, which may be introduced within the canister and/or fluid flow path to improve detection and resolution. In the specific situation of oxygen detection, one may utilize an oxygen sensitive chromophore such as tris(2,2-bipyridyl) dichlororuthenium(II) hexahydrate [Ru(Bpy)]. It is also contemplated herein that one may utilize a phosphorescent dye that is mixed within the fluid exudate and excited using appropriate illumination, such that the phosphorescence lifetime and intensity become indicators of oxygen concentration in the wound environment. In addition, any one or more chromophores identified herein may optionally be encapsulated in microporous beads, having a size (largest linear dimension) of 1.0 nm to 1.0 µm.

Examples of pH chromophores that may be introduced in the exudate fluid may include pH sensitive dyes that exhibit a color shift over a desired pH range. For example, Bromocresol purple changes from yellow to violet between the pHs of 5.2 and 6.8 and Alizarin turns from yellow to red between pHs of 5.6 and 7.1. Other pH indicators may include Bromothymol Blue, Neutral Red, Congo Red, Thymol Blue, etc.

One may also now conveniently and continuously monitor the presence of analytes such as pro-inflammatory cytokines and/or proteases within the wound fluid. Cytokines reference signaling molecules and a relatively large and diverse family of polypeptide regulators of host responses to infection, immune response, inflammation and trauma. Some cytokines act to make disease worse (proinflammatory) whereas others serve to reduce inflammation and promote healing (anti-inflammatory). Interluekin (IL)-1 and (IL)-10 are examples of proinflammatory cytokines and anti-inflammatory cytokines, respectively. Protease may be understood as any enzyme that conducts proteolysis, that is, begins protein catabolism by hydrolysis of the peptide bonds that link amino acids together in polypeptide chains, which form the molecule of a given protein.

With attention again to FIG. 1, it is contemplated that with respect to any analyte that is desired for analysis, one may utilize the indicated microvalves 13 to divert a relatively small amount of fluid from the wound to the indicated microfluidic device 20. Such device may optionally be supplied with labeled antibodies or aptamers to selectively bind to the targeted analyte. In addition, labeled antibodies or aptamers may be introduced into fluid trap 14.

The labeled antibodies or aptamers may themselves include tags that are responsive to sensor 14A. For examples, the tags may be responsive to light energy (e.g. fluorescent tags) or provide electrochemical activity for electrochemical detection. The microfluidic device 20 may include two compartments, 20A and 20B. In the first compartment 20A, the binding of the target analyte may take place with a selected antibody or aptamer. The exudate fluid containing the bound analyte may then be introduced into the second compartment 20B where the bound analytes may be detected. The advantage of utilizing the microfluid device 20 in combination with the NPTD is realized in that only a relatively small amount of antibody or aptamer may be used and as noted herein, the analysis of a selected analyte may be done continuously without disruption of the negative pressure treatment protocol.

As may now also be appreciated, by utilizing and introducing more than one labeled antibody or aptamer, more than one targeted analyte may be identified within the fluid extracted from a wound. For example, it is contemplated herein that one may identify portions of the basic metabolic panel (BMP), which as applied to wound fluid, includes the identification of glucose, calcium, sodium, potassium, carbon dioxide, and/or chloride. In addition, the targeted analyte may include a matrix metallo proteinase, which may be understood as any of a group of endopeptidases that hydrolyze proteins of the extracellular matrix. Finally, the targeted analyte may include bone morphogenic proteins.

In a related embodiment, the present disclosure also relates to the incorporation of an array of optical sensors on the surface of a wound dressing, that may optionally involve a NPTD and negative pressure treatment protocol. Such placement of the optical sensors would then allow for imaging of the wound site which may then provide for the ability to monitor one or more of the following parameters: 1. wound bed circulation; 2. formation of scar tissue; 3. debridement of necrotic tissue; 4. state of wound closure and the amount of epithelialization.

Accordingly, one may incorporate an optical sensor within a wound dressing at the wound location, integrated into the dressing and/or its enclosure, which optical sensor may provide varying wavelengths to monitor selected wound healing events, including fibrosis, or wound biological conditions and/or delivery of drugs, etc. For example, as shown again in FIG. 1, an optical sensor 12A may be positioned to provide the aforementioned information regarding the indicated wound healing parameters. The optical sensor may include multiple fiber bundles to cover all or a portion of the surface area of a given wound area.

One may also now selectively vary the wavelength of light reflected within the wound site such that at wavelengths within the light range of 350 nm-700 nm, and more specifically, at wavelengths of less than or equal to 450 nm (e.g., 350 nm to 450 nm) one may generate scattering of epithelial surface tissue. That is, one may monitor the wound site up to a thickness of about 5.0 mm. Accordingly, one may monitor the formation of fibrin clots, fibroblast development, and collagen incorporation. By contrast, wavelengths of equal to or greater than 600 nm (e.g. 600 nm to 1400 nm) will tend to supply information of underlying tissue properties (e.g., collagen fiber structure, changes such as increase or decrease in blood flow circulation, oxygenation level of the blood supply, etc.). Reference to collagen fiber structure may be understood as reference to a determination of structure at the monomeric level (individual collagen molecules) and/or at the aggregate level (how the amino acids may be arranged or packing structure). That is, in the case of such wavelengths, one may monitor for the indicated parameters up to a thickness of about 3.0 cm. The sensor 12A may specifically include excitation and collection optical fibers integrated in the dressing where the scattering information may then be collected and forwarded to computer device 14C.

In addition, it is contemplated herein that the structural characteristics of the wound may be monitored using reflectance imaging. Structural characteristics may include deposition of collagen fibers, regeneration of stromal (dermal) and epidermal section and fibrosis and development of scars. Accordingly, changes in biochemical structure of tissue will change the reflectance properties, which may now be appropriately monitored.

Furthermore, the optical sensor may be useful in the identification of bacterial biofilm formation (an aggregation of microorganisms on a substrate). This may be based on unique autofluorescence properties of certain bacteria's and biofilms. Such fluorescence may result when cells are excited by either UV radiation (10 nm to 400 nm) or light at wavelengths of 400 nm to 700 nm. Accordingly, the present invention contemplates the use of a fluorescence response at wavelengths of 10 nm to 700 nm.

In addition, as shown in FIG. 1, the present disclosure contemplates the use of sensors 14A either within canister 14 and/or microfluidic device 20 in combination with optical sensor 12A. In such manner, and in combination with a particular negative pressure treatment protocol, one may now generate real time analysis of wound healing, to include, e.g., wound biochemistry, which may include monitoring of wound pH, fluid oxygen levels, presence of absence of targeted analytes, presence or absence of certain portions of the BMP, and the presence of absence of matrix metallo proteinase. Such biochemical evaluation may then be coordinated on a real-time basis with what may be understood as physical would healing characteristics, which as noted, may include an evaluation of epithelial surface tissue development, fibroblast development and/or collagen formation, as applied to either acute of chronic wound healing. This real time data can be used to provide real-time therapy adjustment.

Although the foregoing invention has been described in some detail by way of illustration and example for purpose of clarity and understanding, it will be apparent to those skilled in the art that certain changes and modifications will be practiced. Therefore, the description and examples should not be construed as limiting the scope of the invention, which is delineated by the appended claims

What is claimed is:

1. An apparatus to evaluate and monitor healing progress of a wound and to generate data to modify or identify a treatment protocol comprising:
    a dressing enclosure for administering reduced pressure treatment to a wound, wherein the enclosure is configured to cover the wound and to maintain reduced pressure at the wound location;
    a device capable of supplying reduced pressure;
    a microfluidic device including a closed-channel continuous flow system connected between said dressing enclosure for said wound and said device capable of supplying reduced pressure to withdraw fluid exudates containing one or more analytes from said wound wherein said microfluidic device includes first and second compartments wherein in said first compartment an analyte that is one of said one or more analytes binds with one or more labeled antibodies or aptamers and in a second compartment the bound analyte is detected; and
    a sensor in said second compartment of said microfluidic device capable of analyzing said fluid exudates for one or more analytes indicative of said progress of wound healing and said analyzing of said fluid exudates is done continuously without disruption of said reduced pressure at said wound location and providing real time analysis of wound healing and providing real-time treatment protocol adjustments.

2. The apparatus of claim 1 wherein said closed-channel continuous flow system includes flow passages having a width or dept of 1 μm to 500 μm and wherein said exudate fluid is configured to flow in said flow passages at a rate of 1 μL/min to 100 μL/min.

3. The apparatus of claim 1 wherein said sensor analyzes said fluid exudate and provided an indication of fluid pH.

4. The apparatus of claim 1 wherein said sensor analyzes said fluid exudate and provides an indication of fluid oxygen level.

5. The apparatus of claim 1 wherein said sensor analyzes said fluid exudates for the presence of wherein said sensor analyzes said fluid exudates for the presence of one or more of the following: biomarkers of active bacterial infection, pro-inflammatory cytokines, proteases, and tissue growth factors.

6. The apparatus of claim 1 wherein a pH sensitive chromophore is introduced into said microfluidic device.

7. The apparatus of claim 1 wherein an oxygen sensitive chromophore is introduced into said fluid trap.

8. The apparatus of claim 1 wherein said sensor analyzes said fluid exudates for the presence of one or more of the following: biomarkers of active bacterial infection, pro-inflammatory cytokines, proteases, and tissue growth factors.

9. The apparatus of claim 1 wherein said sensor analyzes said fluid exudate for matrix metallo proteinase.

10. The apparatus of claim 1, further including an optical sensor in said dressing enclosure, wherein said optical sensor is configured to provide varying wavelengths of light to said wound location.

11. The apparatus of claim 1 wherein said optical sensor is configured to provide light at wavelengths of 350 nm to 700 nm.

12. The apparatus of claim 1 wherein said optical sensor is configured to provide light at wavelengths of 600 nm to 1400 nm.

13. A method to evaluate and monitor healing progress of a wound via analysis of wound fluid exudate comprising:
    locating a dressing enclosure for administering reduced pressure treatment to a wound at a wound location, wherein said enclosure is configured to cover said wound and to maintain reduced pressure at the site of the wound;
    supplying a device that provides reduced pressure to said dressing enclosure;
    locating a microfluidic device including a closed-channel continuous flow system between said dressing enclosure for said wound and said device capable of supplying reduced pressure;
    withdrawing fluid exudate from said wound containing one or more analytes wherein said microfluidic device includes first and second compartments wherein in said first compartment an analyte that is one of said one or more analytes binds with one or more labeled antibodies or aptamers and in a second compartment the bound analyte is detected;
    supplying a sensor in said second compartment of said microfluidic device capable of analyzing said fluid exudates for one or more analytes indicative of the progress of said wound healing and said analyzing of said fluid exudates is done continuously without disruption of said reduced pressure at said wound location; and
    identifying one or more of said analytes and providing real time analysis of wound healing and providing real-time treatment protocol adjustments.

* * * * *